United States Patent

Dillon et al.

[11] Patent Number: 5,833,670
[45] Date of Patent: Nov. 10, 1998

[54] PROTECTIVE DEVICE

[75] Inventors: Jagmohanbir Singh Dillon, Bonython; William Leonard Mobbs, Wanniassa, both of Australia

[73] Assignee: Noble House Group, Woden, Australia

[21] Appl. No.: 727,415

[22] PCT Filed: Apr. 20, 1995

[86] PCT No.: PCT/AU95/00224

§ 371 Date: Oct. 18, 1996

§ 102(e) Date: Oct. 18, 1996

[87] PCT Pub. No.: WO95/28979

PCT Pub. Date: Nov. 2, 1995

[30] Foreign Application Priority Data

Apr. 20, 1994 [AU] Australia ................................ PM 5206

[51] Int. Cl.[6] ....................................................... A61M 5/00
[52] U.S. Cl. ........................... 604/263; 604/192; 604/171; 128/919
[58] Field of Search ............................ 128/919; 604/263, 604/110, 164, 192, 165, 198, 171

[56] References Cited

U.S. PATENT DOCUMENTS

| | | | |
|---|---|---|---|
| 4,417,887 | 11/1983 | Koshi | 604/162 |
| 4,917,243 | 4/1990 | Abrams et al. | 206/365 |
| 5,112,313 | 5/1992 | Sallee | 604/192 |
| 5,120,320 | 6/1992 | Fayngold | 604/177 |
| 5,376,075 | 12/1994 | Haughton et al. | 604/158 |

*Primary Examiner*—Wynn Wood Coggins
*Assistant Examiner*—Deborah Blyveis
*Attorney, Agent, or Firm*—Michael D. Bednarek; Kilpatrick Stockton LLP

[57] ABSTRACT

A protective device (2) for a conventional catheter assembly (4) of the type used by blood banks and including a needle mount (12), a forwardly extending needle (10), and a rearwardly extending conduit (14), the protective device comprising: a sleeve member (6) adapted to be slidably supported on the conduit in a first non-shielding position, and adapted to be forwardly displaced relative to the catheter assembly from the first non-shielding position to a second non-shielding position wherein the sleeve member is restrained relative to the catheter assembly, and adapted to be forwardly displaced relative to the catheter assembly from the second non-shielding position to a shielding position wherein the needle is shielded.

1 Claim, 3 Drawing Sheets

PROTECTIVE DEVICE

TECHNICAL FIELD

This invention relates to a protective device for protecting against needle-stick injury by a catheter assembly.

The invention has particular utility with catheter assemblies of the type used by blood banks and the invention will hereinafter be described with reference to such use. However, a catheter assembly, as the term is used herein, may also be used to infuse fluid.

Catheter assemblies of the type referred to above are generally composed of a needle, a needle mount, and a flexible conduit which leads to the blood collection bag. In many instances the catheter assembly is a so-called "wing catheter" and the needle mount includes a pair of laterally extending protrusions or wings.

In use, the medical practitioner manually grasps the needle mount during withdrawal of the needle from the donor and uses the other hand to apply a swab and pressure to the puncture wound. It is desirable to shield the needle as soon as possible with a view to minimising the possibility of needle-stick injury.

BACKGROUND ART

There have been many solutions proposed to the problems presented by needle-stick injury.

The most relevant prior art known to the applicant is WO 92/04063 in the name of Gianakos which discloses a construction including a ratchet and pawl arrangement, the ratchet 20 being disposed on a non-conventional needle mount or body 12.

DISCLOSURE OF THE INVENTION

This invention in one aspect resides broadly in a protective device for a conventional catheter assembly of the type used by blood banks and including a needle mount, a forwardly extending needle, and a rearwardly extending conduit, the protective device comprising:

a sleeve member adapted to be slidably supported on the conduit in a first non-shielding position, and adapted to be forwardly displaced relative to the catheter assembly from the first non-shielding position to a second non-shielding position wherein the sleeve member is restrained relative to the catheter assembly, and adapted to be forwardly displaced relative to the catheter assembly from the second non-shielding position to a shielding position wherein the needle is shielded.

Preferably, the protective device comprises fixing means for fixing the sleeve member in the shielding position.

Preferably, the sleeve member is adapted to be single-handedly displaced from the second non-shielding position to the shielding position.

Preferably, the protective device comprises restraining means for restraining the sleeve member in the second non-shielding position against rearward displacement relative to the catheter assembly.

The restraining means may be disposed on the catheter assembly and adapted to selectively engage the sleeve member. However, it is preferred that the restraining means be disposed on the sleeve member and adapted to engage the catheter assembly.

Preferably, the fixing means and restraining means are cooperable with the needle mount of the catheter assembly to respectively fix and restrain the sleeve member. Alternatively, the fixing means and/or restraining means may cooperate with the conduit or needle to respectively fix and restrain the sleeve member.

The restraining means may include resilient barbs adapted to engage the needle mount, frictional engagement means, abutment means adapted to abut the needle mount, or releasable locking means selectively engageable with the needle mount.

The sleeve member may include a plurality of sub-members. Preferably, a pair of sub-members are hinged together about a longitudinally extending axis, the sub-members adapted to be closed and locked together about the conduit so that the sleeve member is slidably disposed on the conduit.

Preferably, the protective device comprises actuation means adapted to be manually engaged to longitudinally displace the sleeve member towards the shielding position.

In another aspect the invention resides broadly in a protective device and catheter assembly comprising:

a catheter assembly of the type used by blood banks and including a needle mount, a forwardly extending needle, and a rearwardly extending conduit; and a protective device comprising a sleeve member adapted to be slidably supported on the conduit in a first non-shielding position, and adapted to be forwardly displaced relative to the catheter assembly from the first non-shielding position to a second non-shielding position wherein the sleeve member is restrained relative to the catheter assembly, and adapted to be forwardly displaced relative to the catheter assembly from the second non-shielding position to a shielding position wherein the needle is shielded.

BRIEF DESCRIPTION OF THE INVENTION

In order that this invention may be more easily understood and put into practical effect, reference will now be made to the accompanying drawings which illustrate preferred embodiments of the invention, wherein.

BEST MODE

Figure 1A:
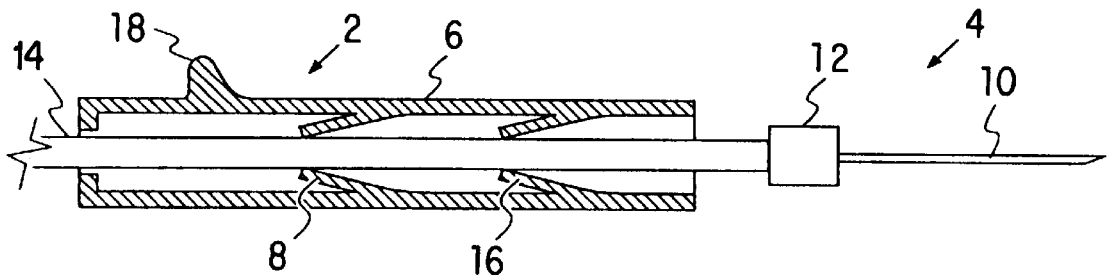
FIG. 1A–1C is a series of three sequential views of a protective device and catheter assembly according to the invention.

Referring to FIG. 1, there is shown a protective device 2 for a catheter assembly 4.

Catheter assembly 4 consists of needle 10, needle mount 12, and conduit 14.

Figure 1B:
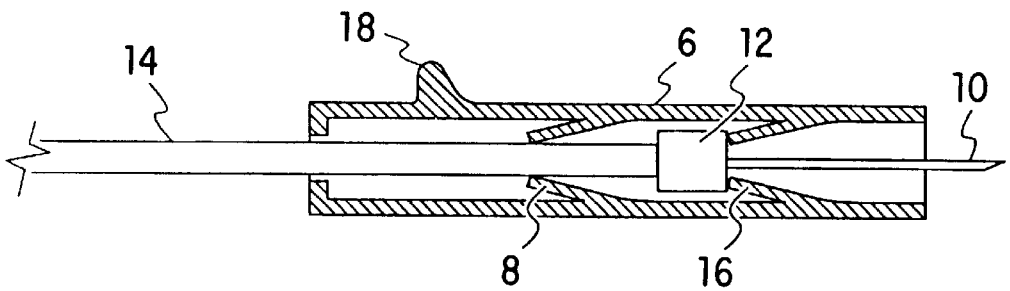
Figure 1C:
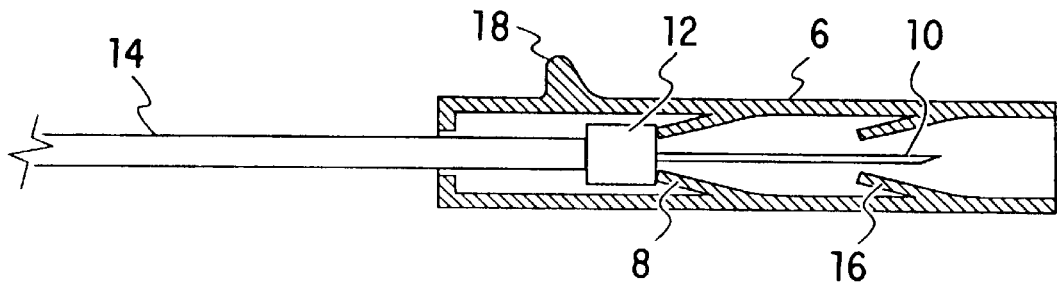

Protective device 2 comprises sleeve member 6 adapted to be restrained in a second non-shielding position on catheter assembly 4 (refer to FIG. 1B) and to be longitudinally displaced relative to catheter assembly 4 from the second non-shielding position to a shielding position (refer to FIG 1C). Sleeve member 6 may be configured such that, when in the shielded position shown in FIG. 1C, needle 10 abuts the side-wall of sleeve member 6. An absorbant material may be adhered to the side-wall of sleeve member 6 to absorb any leakage of blood or other fluid from needle 10 subsequent to use.

Protective device 2 also comprises fixing means 8 for fixing sleeve member 6 in the shielding position.

It will be noted that, when sleeve member 6 is supported on needle assembly 4 as illustrated in FIG. 1B, the medical practitioner can easily displace it to the shielding position illustrated in FIG. 1C. Conveniently, sleeve member 6 is restrained in the second non-shielding position for single-handed displacement i.e. the medical practitioner can grasp conduit 14 in the palm of a hand whilst using the thumb of the same hand to urge sleeve member 6 forward to the shielding position shown in FIG 1C.

Protective device 2 further comprises restraining means 16 for restraining sleeve member 6 in the second non-shielding position (refer to FIG. 1B) against relative longitudinal displacement in at least one longitudinal direction. As can be seen in FIG. 1B, restraining means 16 acts to restrain sleeve member 6 against longitudinal displacement to the configuration shown in FIG 1A. It is important that sleeve member 6 is restrained in a position from which it can be readily deployed, preferably single-handedly, with a view to avoiding needle-stick injury.

Fixing means 8 and restraining means 16 cooperate with needle mount 12 of needle assembly 4 to respectively fix and restrain the sleeve member.

In FIG. 1, restraining means 16 and fixing means 8 take the form of resilient barbs adapted to engage the needle mount. In an alternative arrangement not illustrated, needle mount 12 may be received in a friction fit within sleeve member 6 thereby restraining sleeve member 6 relative to catheter assembly 4 in the second non-shielding position but allowing deployment to the shielding position.

Figure 2:
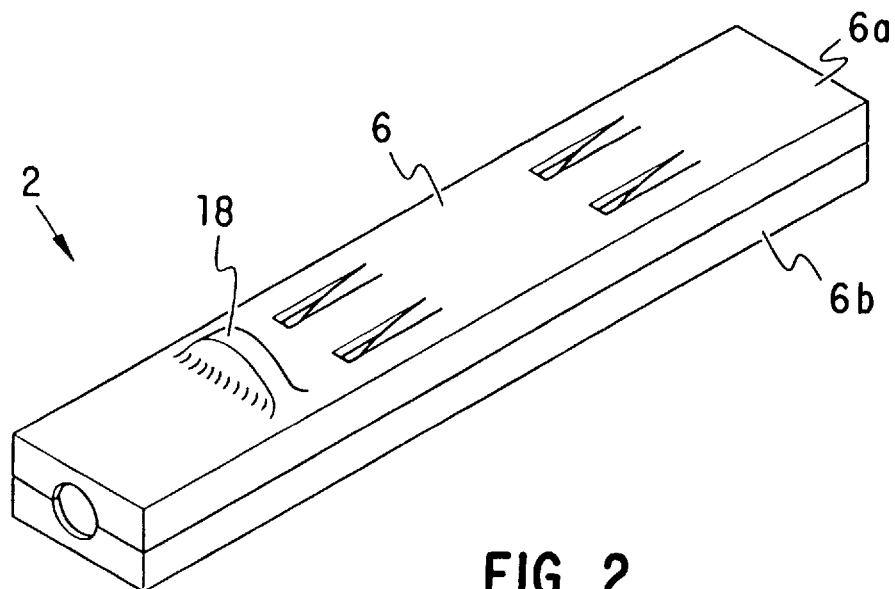
FIG. 2 is a perspective view of the protective device of FIG. 1.

Referring to FIG. 2, sleeve member 6 includes a pair of sub-members 6a and 6b. The sub-members are hinged together along a common longitudinal edge to facilitate simple assembly on conduit 14 as shown in FIG 1A. Thus, protective device 2 need not be integrally manufactured on catheter assembly 4, but rather may be placed on conduit 14 immediately prior to use. Sub-members 6a and 6b may be hinged together only by a small portion adjacent one end of the respective longitudinal edges of the sub-members so that the wing of a wing catheter assembly may freely traverse the length of the longitudinal gap defined between the respective longitudinal edges.

Protective device 2 comprises actuation means 18 adapted to be manually engaged, usually by a thumb, to longitudinally displace sleeve member 6 to the shielding position shown in FIG. 1C.

Whilst FIG. 1 shows restraining means 16 disposed on sleeve member 6, restraining means 16 may, of course, be disposed on catheter assembly 4.

Referring now to FIGS. 3 to 6, there is shown a second embodiment of a protective device according to the invention.

Figure 3:
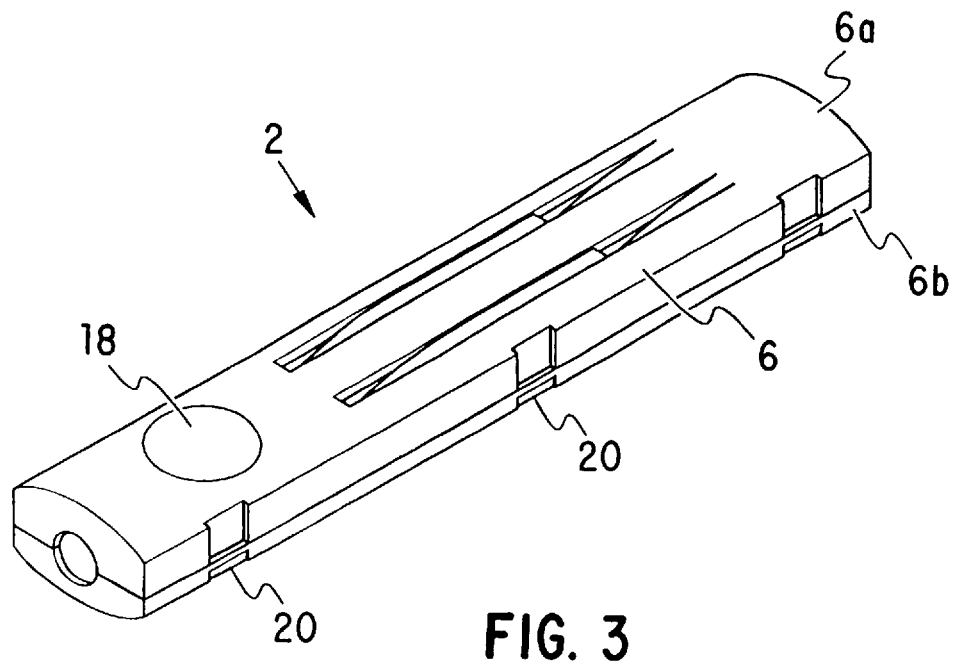
FIG. 3 is a perspective view of a second embodiment of a protective device according to the invention.
Figure 4:
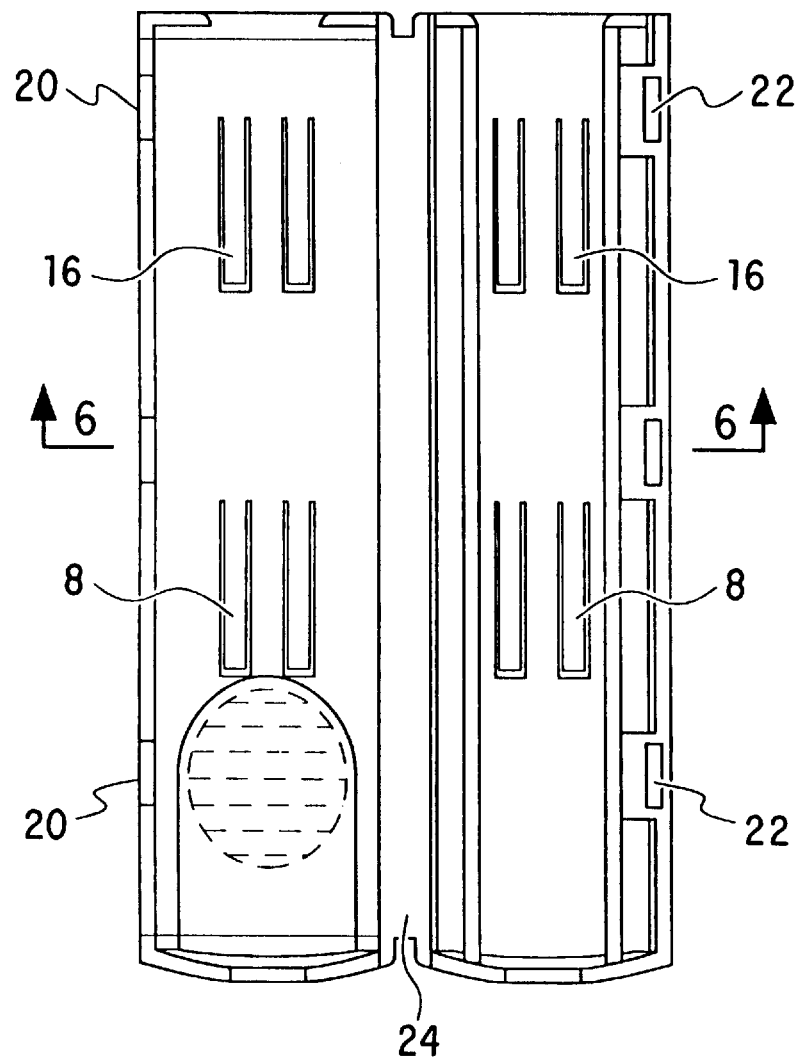
FIG. 4 is a plan view of the protective device of FIG. 3 shown in open configuration.
Figure 5:
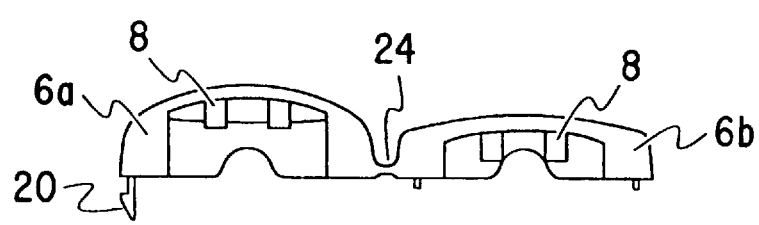
FIG. 5 is an end view for the protective device of FIG. 4.
Figure 6:
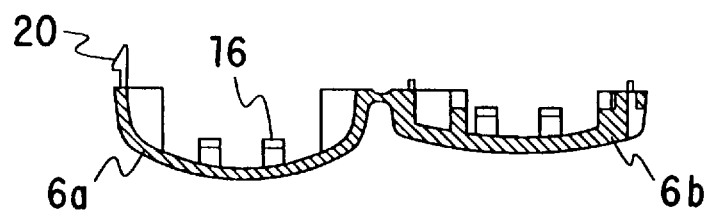
FIG. 6 is a sectional view along line 66 of FIG. 4.

The protective device of FIGS. 3 to 5 includes resilient locking means in the form of a spigot 20 and aperture 22 to lock the sub-members 6a and 6b together over the conduit.

Protective device 2 includes upper and lower sub-members 6a and 6b hinged together about integral hinge 24. Integral hinge 24 is shown as extending the entire length of the protective device. However, the hinge need only extend a small distance from the lower end (refer to FIG. 4) of the device. If only the lowermost locking means is included, two open ended slots are defined between upper sub-member 6a and lower sub-member 6b when in the closed configuration. These slots may slidably receive the wings of a wing catheter.

Upper sub-member 6a includes actuation means 18 in the form of a scalloped portion adapted to receive a thumb.

Lower sub-member 6b is flatter in section than upper sub-member 6b to facilitate the seating and adhering of the protective device 2 against a donor's skin. In this regard, in use, the needle may be inserted into a donor and the protective device displaced along the conduit to the second non-shielding position. In this position, the protective device is "cocked" and ready to be deployed to the shielding position. The protective device is left in the "cocked" or second non-shielding position whilst the donation is completed. It may be taped to the arm of the donor with adhesive tape during the donation. When the donation is complete, the needle may be removed and shielded by removing the adhesive tape, grasping the conduit in the palm of a hand and urging the protective device to the shielding position with the thumb of the same hand. Alternatively, the adhesive may be left in place and the conduit pulled so that the needle is withdrawn from the donor into the protective device which is fixed relative to the donor by the adhesive tape.

In use, the protective device 2 of FIG. 1 is initially slidably positioned in the first non-shielding position on conduit 14 as shown in FIG. 1A. The medical practitioner grasps needle mount 12 and needle 10 is inserted into the donor. Protective device 2 is then urged to the second non-shielding position shown in FIG. 1B whereat it is restrained and is conveniently available for deployment to the shielding position. Upon completion of the donation the medical practitioner grasps the protective device and/or needle assembly in one hand and withdraws needle 10 from the donor whilst using the other hand to apply pressure and a swab to the puncture wound. Actuation means 18 is engaged by the thumb of the one hand and sleeve member 6 is urged to the shielded position illustrated in FIG. 1C. Alternatively, sleeve member 6 may be fixed to the forearm of the donor by adhesive tape or the like. In this arrangement, the medical practitioner may simply pull on conduit 14 to withdraw needle 10 and simultaneously deploy sleeve member 6. It would then be necessary to disengage the sleeve member from the donor's forearm.

The positioning of the sleeve member 6 in the non-shielding position facilitates simple, preferably single handed, deployment of the sleeve member. That is, sleeve member 6 is positioned ready to be deployed and is not free to move to a position from which it must be retrieved before deployment can occur. The provision of restraining means allows a more positive form of positioning. Moreover, because restraining means acts to prevent relative longitudinal displacement of sleeve member 6 with respect to needle assembly 4 in at least one longitudinal direction, the sleeve member 6 may be grasped by the medical practitioner to withdraw needle 10.

It will of course be realised that whilst the above has been given by way of illustrative example of this invention, all modifications and variations hereto, as would be apparent to persons skilled in the art, are deemed to fall within the broad scope and ambit of this invention.

The claims defining the invention are as follows:

1. A protective device for a conventional catheter assembly of the type used by blood banks and including a needle mount, a forwardly extending needle, and a rearwardly extending conduit, the protective device comprising:

a sleeve member adapted to be slidably supported on the conduit in a first non-shielding position, and adapted to be forwardly displaced relative to the catheter assembly from the first non-shielding position to a second non-shielding position wherein the catheter assembly is restrained relative to the sleeve member, and adapted to be forwardly displaced relative to the catheter assembly from the second non-shielding position to a shielding position wherein the needle is shielded;

wherein the sleeve member includes a pair of sub-members;

wherein the sub-members are hinged together about a longitudinally extending axis, the sub-members being adapted to be closed and locked together about the conduit so that the sleeve member is slidably disposed on the conduit.

* * * * *